(12) United States Patent
Burrows et al.

(10) Patent No.: US 12,697,640 B2
(45) Date of Patent: Aug. 4, 2026

(54) ROTARY REACTOR WITH DRUM FOR DEPOSITION OF FILMS ONTO PARTICLES

(71) Applicant: Applied Materials, Inc., Santa Clara, CA (US)

(72) Inventors: Brian Hayes Burrows, San Jose, CA (US); Sekar Krishnasamy, Bangalore (IN); Ayyanagouda Raravi, Bangalore (IN); Monika Mudalkar, Karnataka (IN); Govindraj Desai, Bangalore (IN); Hemantha Kumar Raju, Bangalore (IN); Basavaraj Pattanshetty, Bangalore (IN); David Masayuki Ishikawa, Mountain View, CA (US); Visweswaren Sivaramakrishnan, Cupertino, CA (US); Shrikant Swaminathan, Santa Clara, CA (US); Mario Cambron, San Jose, CA (US); Robert Navasca, Union City, CA (US); Miaojun Wang, Santa Clara, CA (US); Jonathan Frankel, Los Gatos, CA (US)

(73) Assignee: Applied Materials, Inc., Santa Clara, CA (US)

( * ) Notice: Subject to any disclaimer, the term of this patent is extended or adjusted under 35 U.S.C. 154(b) by 688 days.

(21) Appl. No.: 17/971,511

(22) Filed: Oct. 21, 2022

(65) Prior Publication Data

US 2023/0128094 A1 Apr. 27, 2023

(30) Foreign Application Priority Data

Oct. 22, 2021 (IN) .............................. 202141048138

(51) Int. Cl.
*B05C 19/02* (2006.01)
*A61K 9/16* (2006.01)
(Continued)

(52) U.S. Cl.
CPC ............ *B05C 19/02* (2013.01); *A61K 9/1682* (2013.01); *B01J 8/1836* (2013.01); *B01J 8/382* (2013.01);
(Continued)

(58) Field of Classification Search
None
See application file for complete search history.

(56) References Cited

U.S. PATENT DOCUMENTS

| | | | |
|---|---|---|---|
| 3,818,982 A | 6/1974 | Wagner | |
| 4,397,885 A | 8/1983 | Akai et al. | |

(Continued)

FOREIGN PATENT DOCUMENTS

| | | |
|---|---|---|
| CN | 103764267 | 4/2014 |
| CN | 104046958 | 9/2014 |

(Continued)

OTHER PUBLICATIONS

Office Action in Taiwanese Appln. No. 111140214, dated Nov. 2, 2023, 13 pages (with English summary and search report).

(Continued)

*Primary Examiner* — Jethro M. Pence
(74) *Attorney, Agent, or Firm* — Fish & Richardson P.C.

(57) ABSTRACT

A reactor for coating particles includes a rotatable reactor assembly includes a reactor drum configured to hold a plurality of particles to be coated, an inlet tube, and an outlet tube. The drum includes a cylindrical tube, and an inlet-side endplate secured to cover an inlet-side opening of the cylindrical tube and/or an outlet-side endplate secured to cover an outlet-side opening of the cylindrical tube. A stationary gas inlet line is coupled to the inlet tube by a rotary inlet seal, a stationary gas outlet line is coupled to the outlet tube by a rotary outlet seal, and a motor rotates the rotatable reactor assembly. The inlet tube is releasably (Continued)

mechanically secured to the inlet-side endplate and the outlet tube is releasably mechanically secured to the outlet-side endplate.

18 Claims, 8 Drawing Sheets

(51) Int. Cl.

| | |
|---|---|
| *B01J 8/18* | (2006.01) |
| *B01J 8/38* | (2006.01) |
| *B01J 19/00* | (2006.01) |
| *B01J 19/28* | (2006.01) |
| *C23C 16/44* | (2006.01) |
| *C23C 16/455* | (2006.01) |
| *C23C 16/458* | (2006.01) |

(52) U.S. Cl.
CPC ........... *B01J 19/0053* (2013.01); *B01J 19/28* (2013.01); *C23C 16/4412* (2013.01); *C23C 16/4417* (2013.01); *C23C 16/455* (2013.01); *C23C 16/4584* (2013.01)

(56) References Cited

U.S. PATENT DOCUMENTS

| | | | |
|---|---|---|---|
| 5,759,483 A * | 6/1998 | Kemp ..................... C21B 13/08 | |
| | | | 266/257 |
| 6,123,097 A * | 9/2000 | Truong ................. F16K 49/002 | |
| | | | 137/341 |
| 6,613,383 B1 | 9/2003 | George et al. | |
| 6,649,217 B1 | 11/2003 | Gust | |
| 6,914,218 B2 * | 7/2005 | Vernik .................... F27B 17/00 | |
| | | | 118/724 |
| 10,953,380 B1 * | 3/2021 | Lin ...................... B01J 19/1806 | |
| 11,174,552 B2 | 11/2021 | Neikirk et al. | |
| 11,180,851 B2 * | 11/2021 | Neikirk ............. C23C 16/45555 | |
| 11,359,710 B1 | 6/2022 | Martin | |
| 11,545,343 B2 * | 1/2023 | Fan ................... H01J 37/32752 | |
| 2006/0213437 A1 | 9/2006 | Ishizaka et al. | |
| 2011/0116984 A1 | 5/2011 | Rehmat et al. | |
| 2011/0200822 A1 | 8/2011 | Detavernier et al. | |

| | | | |
|---|---|---|---|
| 2012/0145041 A1 | 6/2012 | Walters | |
| 2012/0231615 A1 | 9/2012 | Shiomi et al. | |
| 2013/0059073 A1 | 3/2013 | Jiang et al. | |
| 2014/0127756 A1 | 5/2014 | Bolz et al. | |
| 2015/0125599 A1 | 5/2015 | Lindfors et al. | |
| 2016/0023177 A1 | 1/2016 | Tanaka | |
| 2017/0062191 A1 | 3/2017 | Zafiropoulo et al. | |
| 2017/0186574 A1 | 6/2017 | Gentsch | |
| 2018/0019467 A1 | 1/2018 | Zhu et al. | |
| 2018/0019468 A1 | 1/2018 | Zhu et al. | |
| 2018/0221294 A1 | 8/2018 | Carlsson et al. | |
| 2019/0376181 A1 | 12/2019 | Neikirk et al. | |
| 2020/0208265 A1 | 7/2020 | Hsieh et al. | |
| 2020/0284384 A1 | 9/2020 | Michila et al. | |
| 2020/0335311 A1 | 10/2020 | Fan et al. | |
| 2020/0385860 A1 * | 12/2020 | Hirose ..................... B22F 1/16 | |
| 2022/0064794 A1 | 3/2022 | Neikirk et al. | |
| 2022/0106684 A1 | 4/2022 | Lin et al. | |
| 2022/0106686 A1 | 4/2022 | Lin et al. | |
| 2023/0127489 A1 | 4/2023 | Burrows et al. | |
| 2023/0128094 A1 * | 4/2023 | Burrows ............. C23C 16/4417 | |
| | | | 118/308 |
| 2023/0132290 A1 * | 4/2023 | Burrows ............. C23C 16/4417 | |
| | | | 118/716 |

FOREIGN PATENT DOCUMENTS

| | | |
|---|---|---|
| CN | 205741206 | 11/2016 |
| CN | 107904571 A | 4/2018 |
| CN | 208145924 | 11/2018 |
| CN | 112609169 A | 4/2021 |
| CN | 213669190 | 7/2021 |
| JP | 2007-208096 | 8/2007 |
| JP | 2013-115215 A | 6/2013 |
| JP | 2019-527187 A | 9/2019 |
| TW | I729945 B | 6/2021 |
| WO | WO 2007/123510 | 11/2007 |
| WO | WO 2014/044907 | 3/2014 |
| WO | WO 2018/013991 | 1/2018 |

OTHER PUBLICATIONS

European Search Report in Appln. No. 22884741.4, mailed on Aug. 21, 2025, 15 pages.

* cited by examiner

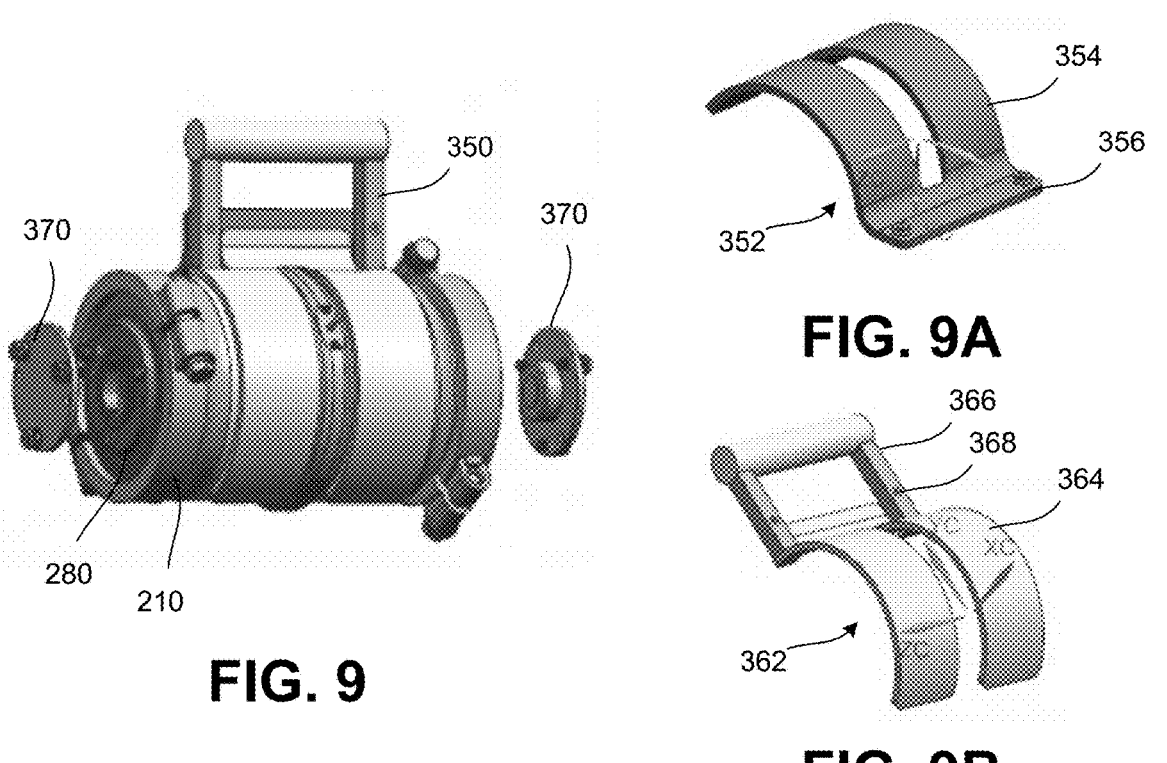
FIG. 9
FIG. 9A
FIG. 9B
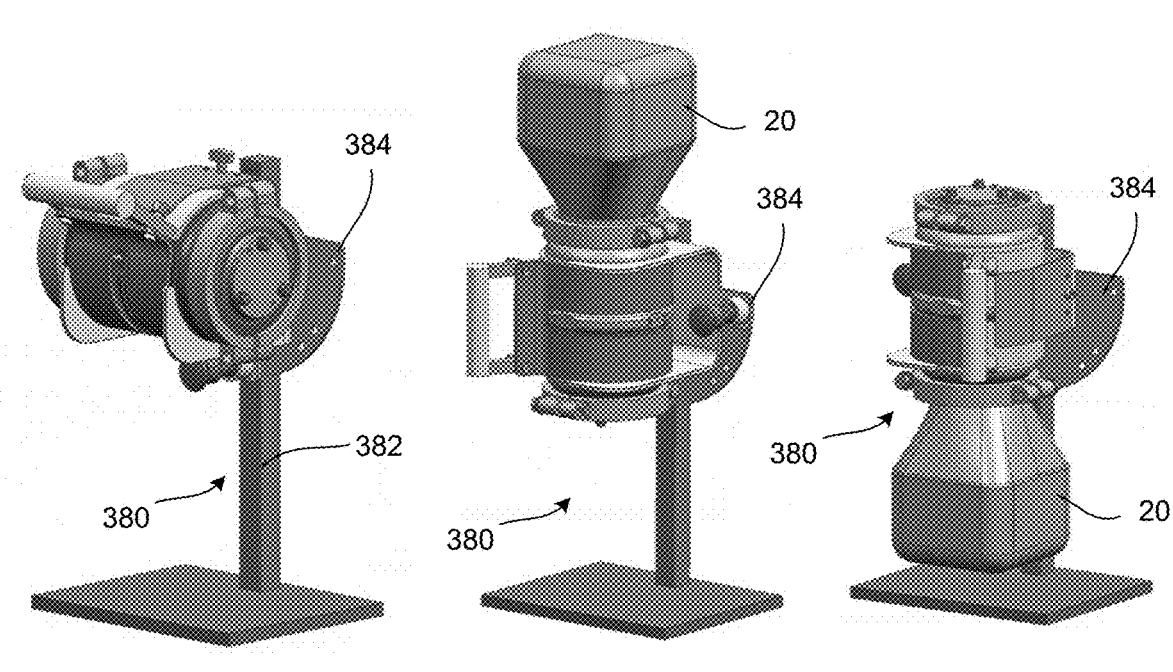
FIG. 10A          FIG. 10B          FIG. 10C

1100

1110

1106

1102

1104

1114

1112

1108

1104

1118

1116

1200

1202

210'

ROTARY REACTOR WITH DRUM FOR DEPOSITION OF FILMS ONTO PARTICLES

TECHNICAL FIELD

This disclosure pertains coating particles, e.g., particles that include active pharmaceutical ingredients, with thin films.

BACKGROUND

It is of great interest to the pharmaceutical industry to develop improved formulations of active pharmaceutical ingredients (API). Formulation can influence the stability and bioavailability of the API as well as other characteristics. Formulation can also influence various aspects of drug product (DP) manufacture, for example, flowability or ease and safety of the manufacturing process.

Numerous techniques for encapsulating or coating API have been developed. Some existing techniques for the coating of API include spray coating, plasma polymerization, hot wire chemical vapor deposition (CVD), and rotary reactors. Spray coating is an industrially scalable technique that has been widely adopted by the pharmaceutical industry. However, coating non-uniformities (both within a particle and from particle to particle) prevent the use of these techniques for improving the delivery profile or stability of active pharmaceutical ingredients (APIs). Particle agglomeration during spray coating also causes significant challenges.

Meanwhile, techniques such as plasma polymerization are difficult to scale, applicable only to certain precursor chemistries, and can result in the degradation of sensitive APIs. Hot wire systems have been developed that utilize a cold substrate as the condensation media for gases and radicals. Rotary reactors include atomic layer deposition (ALD) and initiated CVD (iCVD) reactors. However, ALD reactors are suitable for inorganic coatings and not for organic polymer coatings, and existing iCVD designs do not adequately prevent API degradation and are not scalable for high volume manufacturing. Other techniques include polymer mesh coating, pan coating, aerosolized coating, and fluidized bed reactor coating.

SUMMARY

In one aspect, a reactor for coating particles includes a rotatable reactor assembly including a drum configured to hold a plurality of particles to be coated, an inlet tube, and an outlet tube, a stationary gas inlet line coupled to the inlet tube by a rotary inlet seal, a stationary gas outlet line coupled to the outlet tube by a rotary outlet seal, and a motor to rotate the rotatable reactor assembly.

In another aspect, a reactor drum for coating particles includes a cylindrical tube, an inlet-side endplate covering an inlet-side opening of the cylindrical tube, and an outlet-side endplate covering an outlet-side opening of the cylindrical tube. At least one of the inlet-side endplate or outlet-side endplate is manually removable from the cylindrical tube.

In another aspect, a reactor for coating particles includes a rotatable reactor assembly including a reactor drum configured to hold a plurality of particles to be coated, a lower half-cylinder, an upper half-cylinder that is liftable away from the lower half-cylinder, and a heating element to heat the lower half-cylinder and upper half-cylinder such that the lower half-cylinder and upper half-cylinder radiatively heat the reactor drum.

Implementations may include one or more of the following. At least one of the one or more gaskets may be tri-clover gasket.

In another aspect, a deposition system has an isolator including a glovebox and a window, and a reactor for coating particles. The reactor includes a rotatable reactor assembly positioned within the isolator and viewable through the window and reachable with gloves of the glovebox. The rotatable reactor assembly includes a reactor drum configured to hold a plurality of particles to be coated, an inlet tube, and an outlet tube, and the reactor drum is configured to be detached from the inlet tube and the outlet tube by an operator using the gloves while remaining within the isolator.

Implementations may include, but are not limited to, one or more of the following possible advantages. The process drum containing power can be loaded and unloaded from a rotary actuator and gas supply system while remaining within a sealed environment. This permits use of toxic reactants during deposition and use of more powerful pharmaceutical agents. Various rotary seals can permit the rotary reactor to be operated with lower risk of particulates escaping. Particles can be less likely to spill from the drum during loading and unloading.

Powder that blocks a filter can be removed with a back pulse while also reducing risk of upstream contamination. The assembly can be heated in a uniform manner.

Particles can be coated with thin layer(s), thus providing a drug product with an advantageous volume fraction of API. In addition, the process can result in layer(s) encapsulating the API that are uniform within a particle and from particle-to-particle, providing more consistent properties to the drug formulations.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting.

Other features and advantages of the invention will be apparent from the following detailed description and figures, and from the claims.

BRIEF DESCRIPTION OF THE DRAWINGS

FIG. 9 depicts a handle assembly holding the reactor drum.

FIGS. 9A and 9B depict arcuate portions of first and second components of the handle assembly.

FIGS. 10A-C depict a reactor drum placed on a powder loading/unloading fixture in different configurations.

Like reference numbers and designations in the various drawings indicate like elements.

DETAILED DESCRIPTION

Figure 1:
FIG. 1 is a schematic cross-sectional front view of an example reactor for ALD and/or CVD coating of particles, e.g., drugs, that includes a rotary vacuum chamber, e.g., a drum.

There are various methods for encapsulating API particles. In many cases, these methods result in a coating that is relatively thick. While such coatings can impart desirable properties, the high ratio of coating to API can make it difficult to create a drug product in which the volume fraction of API is as high as desired. In addition, the coating encapsulating the API can be non-uniform, making it difficult to provide formulations with consistent properties.

An approach that may address these issues is to use a rotary "drum" in which particles are subject to tumbling action while process gas is injected into the drum. However, practical implementation of a reliable system suitable for drug manufacturing faces a variety of impediments. As one issue, the either the process gasses used or the pharmaceutical components may be toxic. So simply opening a reactor chamber to remove the coated particulates may be impossible. A more complete solution, which permits the reactor to be cleaned and serviced and powder to be loaded or unloaded, while still preventing release of material from the reactor into the environment and to prevent contamination of the API, is warranted. As another issue, even within a sealed environment, there is a danger of particles fouling gas supply lines. Some techniques would be useful to reduce this danger. As yet another issue, the reactor chamber or powder should heated to a desired temperature for the deposition process. However, uniform heating may be difficult to achieve. As still another issue, some processes may use very small batch sizes, e.g., less than 0.5 L of particles. It would be desirable to have a system that is compatible with multiple reactor sizes. In general, a variety of potentially independently usable features are discussed below that can address one or more of the issues above, or other issues.

Drug

The term "drug," in its broadest sense includes all small molecule (e.g., non-biologic) APIs. The drug could be selected from the group consisting of an analgesic, an anesthetic, an anti-inflammatory agent, an anthelmintic, an anti-arrhythmic agent, an antiasthma agent, an antibiotic, an anticancer agent, an anticoagulant, an antidepressant, an antidiabetic agent, an antiepileptic, an antihistamine, an antitussive, an antihypertensive agent, an antimuscarinic agent, an antimycobacterial agent, an antineoplastic agent, an antioxidant agent, an antipyretic, an immunosuppressant, an immunostimulant, an antithyroid agent, an antiviral agent, an anxiolytic sedative, a hypnotic, a neuroleptic, an astringent, a bacteriostatic agent, a beta-adrenoceptor blocking agent, a blood product, a blood substitute, a bronchodilator, a buffering agent, a cardiac inotropic agent, a chemotherapeutic, a contrast media, a corticosteroid, a cough suppressant, an expectorant, a mucolytic, a diuretic, a dopaminergic, an antiparkinsonian agent, a free radical scavenging agent, a growth factor, a haemostatic, an immunological agent, a lipid regulating agent, a muscle relaxant, a parasympathomimetic, a parathyroid calcitonin, a biphosphonate, a prostaglandin, a radio-pharmaceutical, a hormone, a sex hormone, an anti-allergic agent, an appetite stimulant, an anoretic, a steroid, a sympathomimetic, a thyroid agent, a vaccine, a vasodilator and a xanthine.

Exemplary types of small molecule drugs include, but are not limited to, acetaminophen, clarithromycin, azithromycin, ibuprofen, fluticasone propionate, salmeterol, pazopanib HCl, palbociclib, and amoxicillin potassium clavulanate.

Pharmaceutically Acceptable Excipients, Diluents, and Carriers

Pharmaceutically acceptable excipients include, but are not limited to:

(1) surfactants and polymers including: polyethylene glycol (PEG), polyvinylpyrrolidone (PVP), sodium lauryl sulfate, polyvinylalcohol, crospovidone, polyvinylpyrrolidone-polyvinylacrylate copolymer, cellulose derivatives, hydroxypropylmethyl cellulose, hydroxypropyl cellulose, carboxymethylethyl cellulose, hydroxypropyllmethyl cellulose phthalate, polyacrylates and polymethacrylates, urea, sugars, polyols, carbomer and their polymers, emulsifiers, sugar gum, starch, organic acids and their salts, vinyl pyrrolidone and vinyl acetate;

(2) binding agents such as cellulose, cross-linked polyvinylpyrrolidone, microcrystalline cellulose;

(3) filling agents such as lactose monohydrate, lactose anhydrous, microcrystalline cellulose and various starches;

(4) lubricating agents such as agents that act on the flowability of a powder to be compressed, including colloidal silicon dioxide, talc, stearic acid, magnesium stearate, calcium stearate, silica gel;

(5) sweeteners such as any natural or artificial sweetener including sucrose, xylitol, sodium saccharin, cyclamate, aspartame, and acesulfame K;

(6) flavoring agents;

(7) preservatives such as potassium sorbate, methylparaben, propylparaben, benzoic acid and its salts, other esters of parahydroxybenzoic acid such as butylparaben, alcohols such as ethyl or benzyl alcohol, phenolic chemicals such as phenol, or quarternary compounds such as benzalkonium chloride;

(8) buffers;

(9) Diluents such as pharmaceutically acceptable inert fillers, such as microcrystalline cellulose, lactose, dibasic calcium phosphate, saccharides, and/or mixtures of any of the foregoing;

(10) wetting agents such as corn starch, potato starch, maize starch, and modified starches, and mixtures thereof;

(11) disintegrants; such as croscarmellose sodium, crospovidone, sodium starch glycolate; and

(12) effervescent agents such as effervescent couples such as an organic acid (e.g., citric, tartaric, malic, fumaric, adipic, succinic, and alginic acids and anhydrides and acid salts), or a carbonate (e.g., sodium carbonate, potassium carbonate, magnesium carbonate, sodium glycine carbonate, L-lysine carbonate, and arginine carbonate) or bicarbonate (e.g. sodium bicarbonate or potassium bicarbonate)

Metal Oxide Material

The term "metal oxide material," in its broadest sense includes all materials formed from the reaction of elements considered metals with oxygen-based oxidants. Exemplary metal oxide materials include, but are not limited to, aluminum oxide, titanium dioxide, iron oxide, gallium oxide, magnesium oxide, zinc oxide, niobium oxide, hafnium oxide, tantalum oxide, lanthanum oxide, and zirconium dioxide. Exemplary oxidants include, but are not limited to, water, ozone, and inorganic peroxide.

Atomic Layer Deposition (ALD)

Atomic layer deposition is a thin film deposition technique in which the sequential addition of self-limiting monolayers of an element or compound allows deposition of a film with thickness and uniformity controlled to the level of an atomic or molecular monolayer. Self-limited means that only a single atomic layer is formed at a time, and a subsequent process step is required to regenerate the surface and allow further deposition.

Molecular Layer Deposition (MLD)

Molecular layer deposition is analogous to atomic layer deposition but using organic precursors and forming organic thin films. During a typical MLD process two homo-bifunctional precursors are used. A first precursor is introduced into a chamber. The molecules of the first precursor react with reactive groups on the substrate surface via the corresponding linking chemistry to add a molecular layer of the first precursor on the substrate surface with new reactive sites. After purging, a second precursor is introduced and the molecules of the second precursor react with the new reactive sites provided by the first precursor generating a molecular layer of the first precursor linked to the second precursor. This is followed by another purge cycle.

Reactor System

Figure 2A:
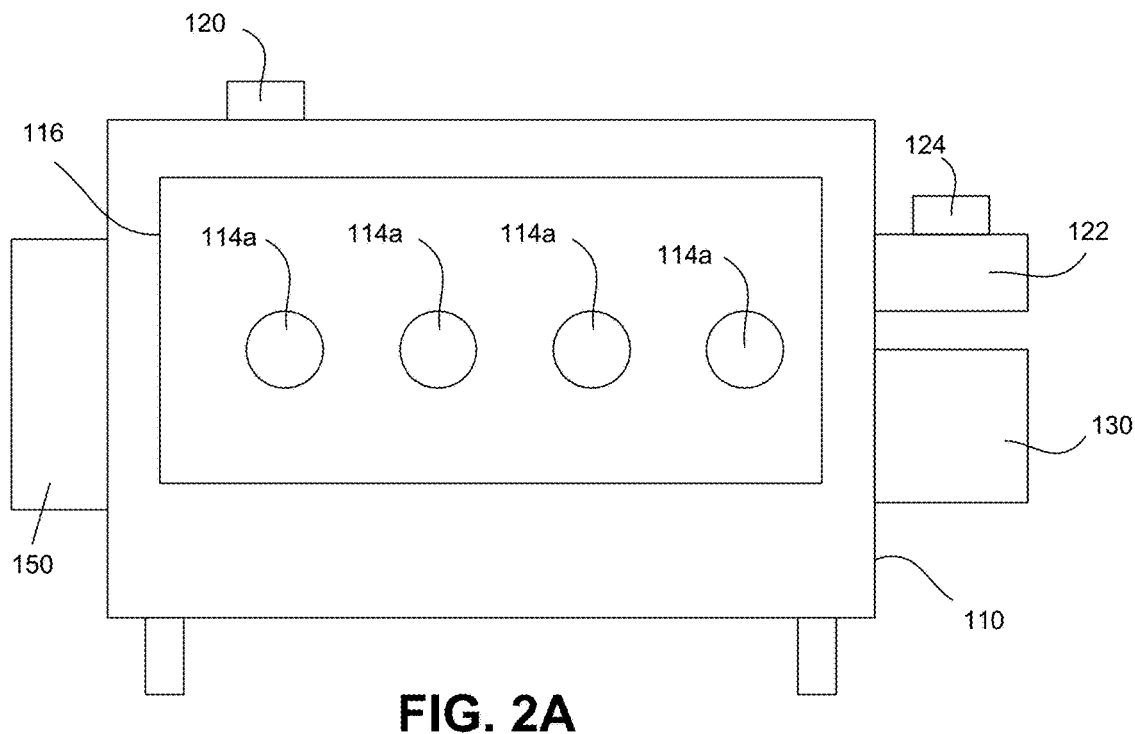
FIG. 2A is a schematic side view of the reactor of FIG. 1.
Figure 2B:
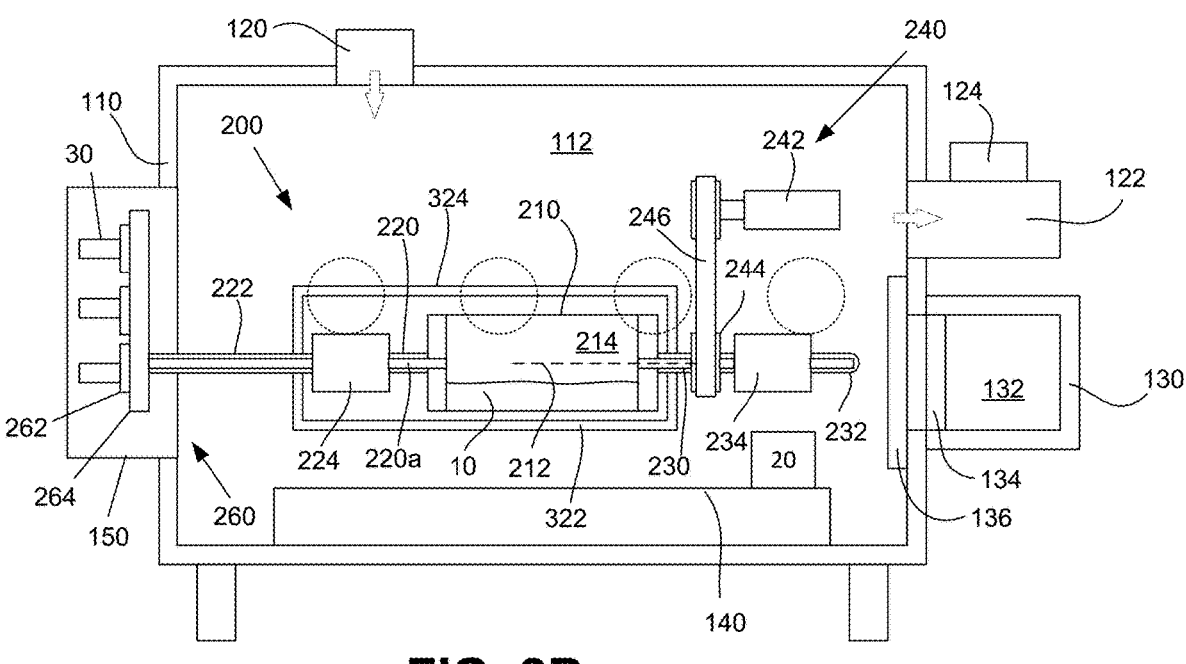
FIG. 2B is a schematic cross-sectional side view of the reactor of FIG. 1. The view of FIG. 2B can be taken along line A-A in FIG. 1.

FIGS. 1, 2A and 2B illustrate a deposition system 100 for coating particles with a thin-film coating. The deposition system 100 includes reactor system 200 which has a rotary cylindrical reactor tube 210 (also referred to as a "drum") which can be partially filled with particles 10 to form a particle bed. In brief, as the reactor drum rotates, one or more process gasses are injected into the drum through an inlet port and exhausted from the drum through an outlet port. Thus, particles 10 in the drum undergo tumbling agitation so that the gasses can be applied uniformly to the particles and deposit a layer on the particles. The particles can have an average or median size (PSD D50) between 0.5 µm and 200 e.g., between 2 µm and 200 e.g., between 5 µm and 100 µm.

The deposition system 100 also include an isolator 110 that forms an isolated chamber 112. At least some components of the reactor system, including at least the reactor tube 210, are located in the chamber 112 of the isolator 110. The isolator 110 can be a glovebox that includes one or more, e.g., four, gloves 114 (ports 114a for the gloves are shown in FIG. 2A). A front panel 116 of the isolator 110 can be transparent, e.g., formed of monolithic tempered glass, so that an operator can view the interior chamber of the isolator 110. In addition, the gloves 114 are positioned so that the operator can manipulate parts of the reactor system 200, e.g., to remove a reactor tube 210 containing coated particles after the deposition process from other portions of the reactor system 200, and to install a new reactor tube with uncoated particles for a subsequent deposition process. The isolator 110 can provide ISO 10648-2 Class-2 containment against leaks and/or containment for APIs up to OEB5 toxicity levels.

The isolator 110 can include an air intake port 120 with an H14 HEPA filter to filter air entering the interior chamber 112, and an exhaust pump 122 connected to an air outlet port 124, also with an H14 HEPA filter. Although FIG. 1 illustrates the outlet port 125 returning air to the environment around the isolator 110, this is not required; the port 125 could be coupled directly to facility exhaust line for further processing. The exhaust pump operates to bring the interior chamber 112 to about −50 Pa to −100 Pa relative to the surrounding pressure in the environment around the isolator 110. Additionally, the isolator can be configured for aseptic operation at pressures slightly above atmospheric pressure, e.g., 2-20% above atmospheric pressure. In some implementations, a polished hygienic stainless steel filter housing can be used with a USP Class VI 0.2 µm exhaust filter. Additionally or alternatively, an oxidizer ampoule heater can heat $H_2O$ up to 135° C. for sterilization. Sterilization can follow refilling the ampoule, and periodically as needed.

As shown in FIGS. 2A and 2B, the isolator 110 also includes a rapid transfer port. In particular, the rapid transfer port includes a detachable transfer container 130 with an interior space 132. The transfer container can be sealed by a valve 134, and similarly the access port connecting the container 130 to the isolator 110 can be sealed by a valve 136. When both valves 134, 136 are open, the interior space 132 of the container 130 can be accessed by an operator using a glove 114. For example, the reactor drum 210 could be placed into transfer container 130. As another example, coated particles could be transferred inside the isolator 110 from the reactor drum 210 into a canister 20, and then the canister could be placed by the operator (using a glove 114) into the container 130. When both valves 134, 136 are closed, the canister 130 can be manually detached from the isolator so that the contents can be transported to another location, e.g., for removal of coated particles from the drum, or for further processing of the particles such as mixture with excipients, pressing into a tablet, or encapsulation in a shell, without danger of contamination of the coated particles or the interior of the isolator 110.

The interior 112 of the isolator 110 can also include a stand or platform 140 to support various components, e.g., parts of the reactor system 200 or tools used for assembly or disassembly of the reactor system 200 or for transfer of powder, within reach of the operator using a gloves 114. For example, the canister 20 could be placed on the platform 140.

As illustrated in FIG. 1, some portions of the deposition system 100, e.g., the isolator 110 and the rotatable reactor drum 210, can be located in a cleanroom 102. In contrast, some other portions of the deposition system 100, e.g., a vacuum pump 250 for the reactor system 200 and an electrical cabinet 310 can be located in a technical area 104 at a much lower level of cleanliness than the cleanroom 102. The cleanroom 102 can be separated from the technical area by a partition wall 106. A controller 300, e.g., a programmed general purpose computer, can be located in the technical area 104 for the operator to control operation of the reactor system 200. In some implementations, the user interface for the controller 300, e.g., a touch screen display, keyboard, etc., is located in the cleanroom 102.

Figures 11A, 11B:
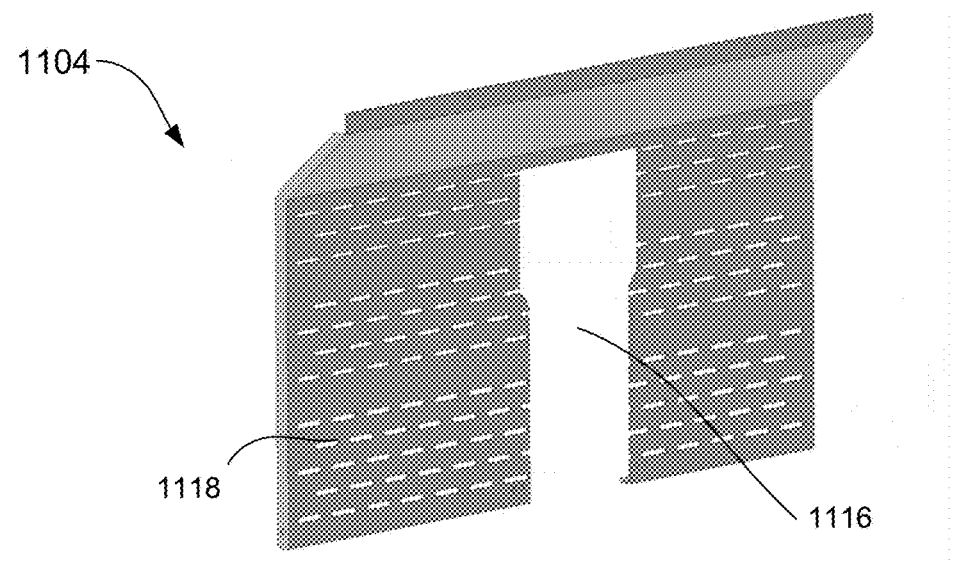
FIG. 11A depicts a fume hood for lowering toxicity compounds.
FIG. 11B depicts a rear panel of the fume hood.

In some implementation, a fume hood is used additionally or alternatively to an isolator 110. FIG. 11A depicts a fume hood 1100 for lowering toxicity of compounds being processed. FIG. 11B depicts a rear panel 1104 of the fume hood 1100. In some implementations, the fume hood 1100 can comply with OEB3 toxicity level standards.

The fume hood 1100 includes a base 1114, side walls 1112, and a hood 1110. The fume hood can be modified from a conventional fume hood to provide a gas inlet 1102, e.g., in a side wall 1112. A sash 1106, which can be a transparent sheet to permit an operator to view the interior of the fume hood 1100 while manipulating equipment therein, extends downwardly from the hood 1110 at the front of the fume hood.

A gap between the base 1114 and the sash 1106 provides an opening 1108 for the operator to reach inside the hood to manipulate equipment. In addition, air can flow in through the opening 1108 and be contained within the interior volume of the fume hood 1100. The fume hood 1100 is configured to maintain constant and uniform air flow through the opening in the sash 1106 by generating negative pressure within the fume hood 1100. The air flows around installed portions of the deposition system 100 and is removed through exhaust holes 1118 in the rear panel 1104. The size of the exhaust holes 1118 can be designed to maintain uniform flow and reduce the chance of fumes containing contaminants recirculating. Contaminants from the air and/or exhausted by the deposition system 100 are filtered before exiting the fume hood 1100.

The rear panel 1104 can be modified to allow exhaust ports and power feedthroughs of the deposition system 100 through an aperture 1116.

Returning to FIG. 1, the controller 300 is configured to operate the reactor system 200 in accord with a "recipe." The recipe specifies an operating value for each controllable element as a function of time. For example, the recipe can specify the times during which the vacuum source 250 is to operate, the times of and flow rate for each gas source, the rotation rate of the rotary reaction drum 210 as set by the motor 242, etc. The controller 170 can receive the recipe as computer-readable data (e.g., that is stored on a non-transitory computer readable medium).

Referring to FIG. 2B, the reactor system 200 will be further described. The reactor system 200 includes the rotatable reactor drum 210, a rotatable inlet tube 220, and a rotatable outlet tube 230. The rotatable inlet tube 220 and the rotatable outlet tube 230 are co-linear with the axis of rotation 212 of the rotatable reactor drum 210. The rotatable inlet tube 220 is fluidically coupled to a stationary inlet line 222 by an inlet rotary seal 224, and the rotatable outlet tube 230 is fluidically coupled to a stationary outlet line 232 by an outlet rotary seal 234. The rotary seals 224, 234 can reduce the risk of escape of particles from the reactor system 200.

For the rotary seals 224, 234, one option would be to use a labyrinth seal. In general, the circuitous path in a labyrinth seal can provide many opportunities for particles to adhere to a seal surface. A labyrinth seal may help maintain vacuum without need of external purge gas.

Another option for the rotary seals 224, 234 is a double cartridge mechanical seal. Such a mechanical seal can include a pair of bearings. In each bearing, an inner ring makes physical contact with an outer ring. Because the rings are in physical contact, the relative motion can result in wear, so the rings can be formed of a non-toxic material that will not interfere with the deposition process, e.g., graphite, or a ceramic with very low wear rate. A purge gas can be injected into the space between the pair of bearings to prevent atmospheric leakage into the reactor. For example, pressure of the purge gas can be controlled from less than 10 mtorr to 30 psig to avoid $N_2$ leakage into reactor and to prevent contamination from air.

The rotatable outlet tube 230 can also function as a drive shaft for the rotatable reactor drum 210. In particular, a rotary drive system 240 includes a drive motor 242 to rotate the rotatable components, e.g., reactor drum 210, a rotatable inlet tube 220, and a rotatable outlet tube 230. A drive wheel 244 is fixed to the rotatable outlet tube 230 at a spot between the reactor drum 210 and the outlet rotary seal 234. The drive wheel 244 is coupled to the motor 242 by a drive belt 246. In operation, the drive motor system 240 can rotate the reactor drum 210 at 1 to 50 rpm, e.g., 6 to 50 rpm. Motion of the reactor drum 210 can be clockwise (CW), counterclockwise (CCW), or can alternate between CW and CCW.

Figures 3, 4, 4A, 5:
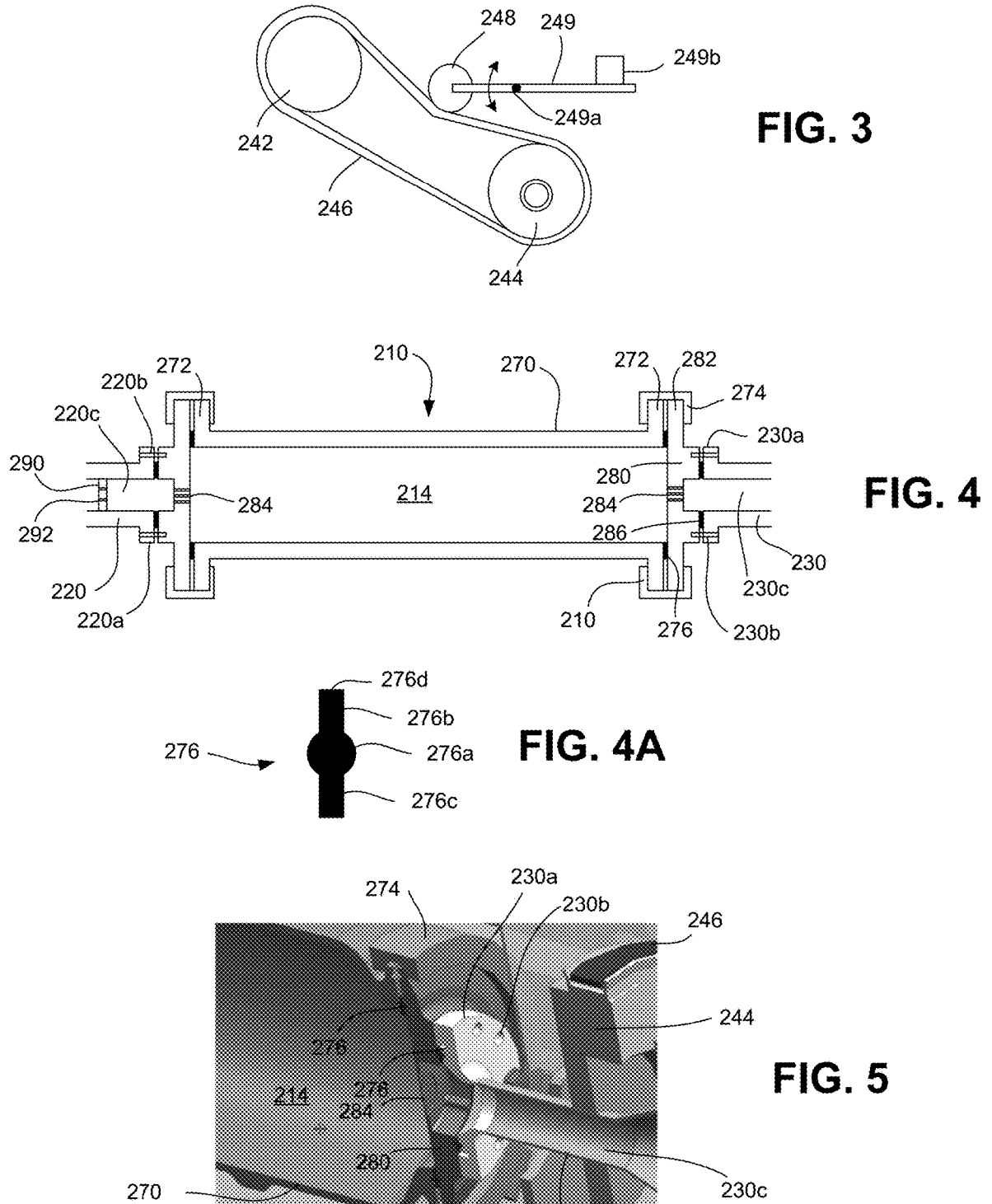
FIG. 3 is a schematic side view of a portion of a drive system for rotating a reactor drum.
FIG. 4 is a schematic cross-sectional side view of a reactor drum assembly.
FIG. 4A is a schematic close-up side view of a gasket.
FIG. 5 is a schematic cross-sectional perspective view of a reactor drum assembly.

FIG. 3 is a schematic side view of a portion of a drive system for rotating a reactor drum. Referring to FIGS. 2B and 3, tension on the drive belt 146 can be adjustable. In particular, the drive belt 246 can have some slack, and the drive system 240 can include a tension wheel 248 that is movable by a control rod 249 into and out of contact with the drive belt, into an out of contact with the outside surface of the drive belt 246. For example, the control rod 249 can be rotatable about a pivot point 249a. A retention mechanism such as detents or clips 249b can hold the control rod 249 in a desired position to apply a predetermined tension to the drive belt 246. Tension on the belt can be released, e.g., by disengaging the control rod 249 from the retention mechanism, in order to permit the rotatable outlet tube 230 and outlet seal 234 to be moved along the axis of rotation 212 away from the reactor drum 210, which permits the reactor drum 210 to be removed from the rest of the reactor system 200. Once a new process tube is installed, the control rod 249 can be moved back into position to couple the motor 242 to the drive shaft 230.

Returning to FIG. 1, the system 100 includes a vacuum source 250 (e.g., one or more vacuum pumps) coupled to the outlet line 232. The vacuum source 250 can be an industrial vacuum pump sufficient to establish pressures less than 1 Torr, e.g., 1 to 100 mTorr, e.g., 20 to 100 mTorr. In some implementations, the vacuum pump can establish a pressure less than 1 atm but above 1 Torr, e.g., 1 to 100 Torr. The vacuum source 250 permits the interior 214 of the reactor drum 210 to be maintained at a desired pressure, and permits removal of reaction byproducts and unreacted process gases.

In some implementations, a purge gas source 252 is connected to the outlet line 232, e.g., to create a backpressure to remove powder blockage of the reactor drum end caps discussed below. The purge gas can be, for example, argon or nitrogen. One or more valves 254 can be used to control whether the vacuum source 250 or the purge gas source 252 is coupled to the outlet line 232.

An ultra-low particulate air filter 258 can be plated in outlet line 232 between the vacuum source 250 and the outlet rotary seal 234 to prevent powder contamination downstream of the filter housing. In some implementations, the ultra-low particulate air filter 258 can be a hygienic Parker demi stainless steel filter housing with a 0.2 μm Tetpor Air Filter Cartridge that meets USP Class VI standards. The housing can have additional polishing on the surfaces upstream of the filter to a 0.4 roughness (Ra) surface finish, and O-rings, e.g., USP Class VI Viton O-Rings, can be used for sealing of joints between parts. The upstream surfaces of the ultra-low particulate air filter 258 can be in contact with the API, so having surfaces that can be adequately cleaned can prevent biologic contamination.

A chemical delivery system 260 includes multiple fluid sources coupled by respective delivery tubes and controllable valves to the inlet line 222. The chemical delivery system 260 injects the fluid in a vapor form into the reactor drum 210. The chemical delivery system 260 include a combination of restrictors, gas flow controllers, pressure transducers, and thermal mass flow controllers/meters to provide controllable flow rate of the various gasses into the reactor drum 210. The chemical delivery system 260 can also include one or more temperature control components, e.g., a heat exchanger, resistive heater, etc., to heat or cool the various gasses before they flow into the reactor drum 210.

As shown in FIG. 2B, an ampule cabinet 150 can be located adjacent the isolator 110. The ampule cabinet 150 includes a portion of the chemical delivery system 260 for the reactor system 200. In particular, located in the ampule cabinet 150 are one or more ports 262 configured to receive one or more ampules 30 containing precursors for the CVD or ALD process, e.g., in gas or liquid form. For example, the ampule cabinet 150 can include three ports 262: two for chemistries and one for an oxidizer. The chemistries can be, for example, trimethylaluminum (TMA), diethanolamine (DEA), titanium tetrachloride ($TiCl_4$), silicon tetrachloride ($SiCl_4$), or) and diethyl zinc (DEZ) vapor. The ports can be coupled by a manifold 264 that can include the various delivery tubes and controllable valves to control flow to the inlet line 222.

In some implementations, the chemical delivery system 260 can include five fluid sources. Two of the fluid sources can provide the two chemically different precursors or reactants for the deposition process for forming a metal oxide layer on the particles. For example, the first fluid source can provide trimethylaluminum (TMA) or titanium tetrachloride ($TiCl_4$), whereas the second fluid source 138b can provide water. Another two of the fluid sources can provide the two chemically different precursors or reactants for the deposition process for forming a polymer material on the metal oxide layer. One of the fluid sources, e.g., the fifth fluid source, can provide an inert gas, e.g., argon or $N_2$, for purging between cycles or half-cycles in the deposition process. Use of more gas sources could enable formation of an even wider variety of laminate structures.

Returning to FIG. 1, the mass flow of the chemistry to the reactor can sensed by a mass flow meter 256, e.g., in the inlet line 232. The mass flow meter 256 can send a signal indicating the mass flow rate to the controller 300, and the controller 300 can control the valves based on the received signal to establish a desired mass flow rate, thus providing a mass flow controller.

The mass flow meter 256 can be a thermal mass flow meter. Such a thermal mass flow meter senses changes in temperature in order to determine mass flow rate. Different materials have different calibration constants, e.g., different partial pressures as a function of temperature. The calibration constant needs to be programmed into the thermal mass flow meter to properly convert a temperature measurement to a mass flow measurement. However, the calibration constant for TMA has been determined through empirical measurement and been found to be unexpectedly low, e.g., an Antoine vapor pressure ranging from about 9 Torr at 20° C. to about 16 Torr at 30° C., which is about half that of water or DEZ. Due to the unusually low calibration constant, the mass flow controller itself may need to be customized, e.g., for orifice size and flow rate range. This can enable a high flow rate using a low vapor pressure source.

Referring to FIGS. 4 and 5, the rotary reactor drum 210 can include a generally cylindrical tube 270 and two generally circular endplates 280, each endplate 280 covering one end of the tube 270. In particular, each end of the cylindrical tube 270 can have an outwardly extending annular flange 272, and the flange 272 can be clamped to the rim 272 of the adjacent endplate 280 by a clamp ring 274.

In some implementations, the inner surface of the tube 270 is a generally smooth and featureless surface; no ridges or similar texturing need be present to assist in agitation of the particles. This may be preferred to make removal of the coated particles from the reactor drum 210 easier. Similarly, the interior of the drum lacks other mechanical features to direct or agitate the powder, e.g., there are no paddles to stir the powder or scraper to remove powder from the inside surface of the tube 270. A cross-section of the tube 270 (e.g., as viewed along the central axis of the cylinder) can be uniform along most, e.g., 80-90%, of the length of the tube 270 (the length is along the central axis 212). This can help ensure uniform gas flow along the length of the reactor drum 210.

An annular seal 276, e.g., a gasket such as a tri-clover gasket, can be clamped between the flange 272 and the rim 272 of the endplate 280. A standard O-ring can create a crevice between the rounded edge of the O-ring and the body being sealed, and particulates can become lodged in this crevice, which can create a danger of later contamination. In contrast, as shown in FIG. 4A, although the annular seal 276 can include a rounded annular central portion 276a that fits within a corresponding recesses in the flange 272 and endplate 280, the inner and outer rim portions 276b, 276c of the annular seal 276 are flat sheets that end in a flat edge surface 276d. Returning to FIGS. 4 and 5, the diameter of the inner rim portion of the annular seal 276 can match the diameter of the end of the inner surface of the cylindrical tube 270. Aligning the annular seal 276 and the end of the inner surface of the cylindrical tube 270 can avoid creation of a recess or gap where particulates can accumulate. In addition, because the edge surface 276d of the inner rim portion 276b is itself flat, no crevice is formed between the seal 276 and the tube 270 or endplate 280.

The rotatable inlet tube 220 can end in a flange 220a that can be secured to the inlet-side endplate 280 by screws 220b that fit through holes in the flange 220a into threaded receiving holes in the inlet-side endplate 280. Small apertures 284, as seen in FIG. 4, are formed through a center portion of the inlet-side endplate 280 and aligned with the passage 220c through the rotatable inlet tube 220 to permit gas to flow from the passage 220d and into the interior 214 of the reactor drum 210. Similarly, the rotatable outlet tube 230 can end in a flange 230a that can be secured to the outlet-side endplate 280 by screws 230b that fit through holes in the flange 230a into threaded receiving holes in the outlet-side endplate 280. Small apertures 284 are formed through a center portion of the outlet-side endplate 280 and aligned with the passage 230c through the rotatable outlet tube 230 to permit gas to flow out of the interior 214 of the reactor drum 210 and into the passage 220d. Two gaskets 286, each similar to the gasket 276 described above, e.g., as a tri-clover gasket, can be used to seal the endplates 280 to the respective flanges 220a, 230a of the inlet tube 220 and outlet tube 230.

The apertures 284 need not be narrower than the particle size, but rather serve to generally prevent large-scale migration of the particles in order to reduce powder loss when the reactor drum 210 is removed from the inlet tube 220 and outlet tube 230.

Due to the flow of gas through the reactor drum 210, particulates can tend to accumulate and clog the apertures 284 in the outlet-side endplate 280. As noted above, backpressure can be applied to the outlet line 232 to blow powder out of the apertures. However, this can create a risk of particulates entering the inlet tube 220. To reduce this risk, an additional powder blocking plate 290 can be positioned in the inlet tube 220 upstream of inlet-side endplate 280. This blocking plate 290 also includes apertures 292 to permit gas flow, but can function to block powder migration during the back pulse.

Figures 6, 7:
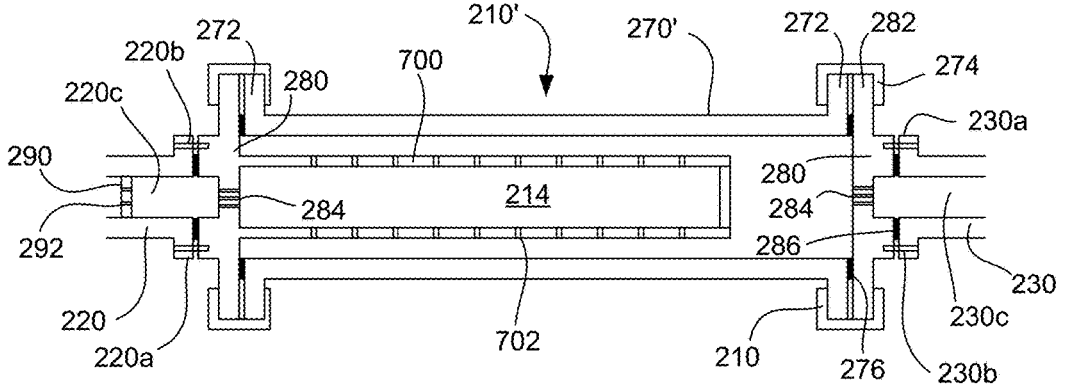
FIG. 6 is a schematic cross-sectional side view of a heating assembly in an open position.
FIG. 7 is a schematic cross-sectional side views of another implementation of a reactor.

Referring to FIGS. 1, 2B, and 6, the deposition system 100 also includes a heater assembly 320 to control the temperature of at least the reactor drum 210. The heater assembly 320 can include two half-cylindrical blocks, a lower half-cylindrical block 322 and an upper half-cylindrical block 324. Embedded in or placed on the surface of each cylindrical block 322 are one or more heating elements 330, e.g., a resistive heater with power supplied from the electrical cabinet 310. Each cylindrical block can be formed of a heat-sink material, e.g., anodized aluminum.

In operation, the lower half-cylindrical block 322 and an upper half-cylindrical block 324 are in the closed position, e.g., as shown in FIG. 1, to surround the reactor drum 210. The heating blocks 322, 324 are conductively heated by the heating elements 330, and the reactor drum 210 and its contents are radiatively heated by heat radiating from the heating blocks 322, 324.

In some implementations, the lower and upper half-cylindrical blocks 322, 324 are connected by one or more hinges 326 along one adjacent edge so that they can open in a clam-shell manner, e.g. as shown in FIG. 6. This permits the operator to access the portion of the reactor system, e.g., the reactor drum 210, for removal or reinstallation. In some implementations, removable heat shields 340 are installed around the lower and upper half-cylindrical blocks 322, 324. The heat shields 340 can be made from metal and reduce the time and power expended to reach stable temperatures when installed.

As shown in FIG. 2B, the heating assembly 320 can extend laterally along the axis of rotation 212 to cover both the rotary inlet seal 224 and the reactor drum 210. Covering the inlet seal 224 permits the heating assembly 320 to preheat the process gas before the gas reaches the reactor drum 210. However, the heating assembly 320 does not cover the rotary outlet seal 234 or the drive wheel 244; the gas does not need to be heated once it is down-stream of the reactor drum 210.

Although FIG. 2B illustrates the lower and upper half-cylindrical blocks 322, 324 as uniform diameter or thickness along the rotation axis 212, this is not necessary. In particular, the inner surface of the lower and upper half-cylindrical blocks 322, 324 can be "form fitting," e.g., can extend inwardly to maintain to be close without touching, e.g., within 1 inch, of the components of the reactor system 200. This can improve radiative heat transfer from the blocks 322, 324 to the rotary inlet seal 224 and the reactor drum 210.

FIG. 7 is a schematic cross-sectional side views of another implementation of a reactor. This implementation is similar to the implementation discussed above, but formed as part of or attached to the inlet-side endplate 280 is a porous cylindrical inner tube 700 that fits within the outer tube 270'. For example, apertures 702 can be formed through the cylindrical surface of the inner tube 700. The apertures can be about 5-10 microns in. In operation, particles are loaded into the inner tube 700. The process gas can flow into the inner tube 700 through the apertures 284 in the inlet-side endplate 280, through the powder bed in the inner tube 700 (which rotates with the reactor drum 210), and into the space between the outer tube 270' and the inner tube 700, and then out through the apertures 284 in the outlet-side endplate 280.

This configuration can permit a reactor drum 210' with a smaller interior volume to hold the particles, but which is otherwise mechanically compatible with the overall reactor system 200. For example, the reactor drum 210' can be mounted onto the same rotatable inlet tube 220 and outlet tube 230.

Figure 12A:
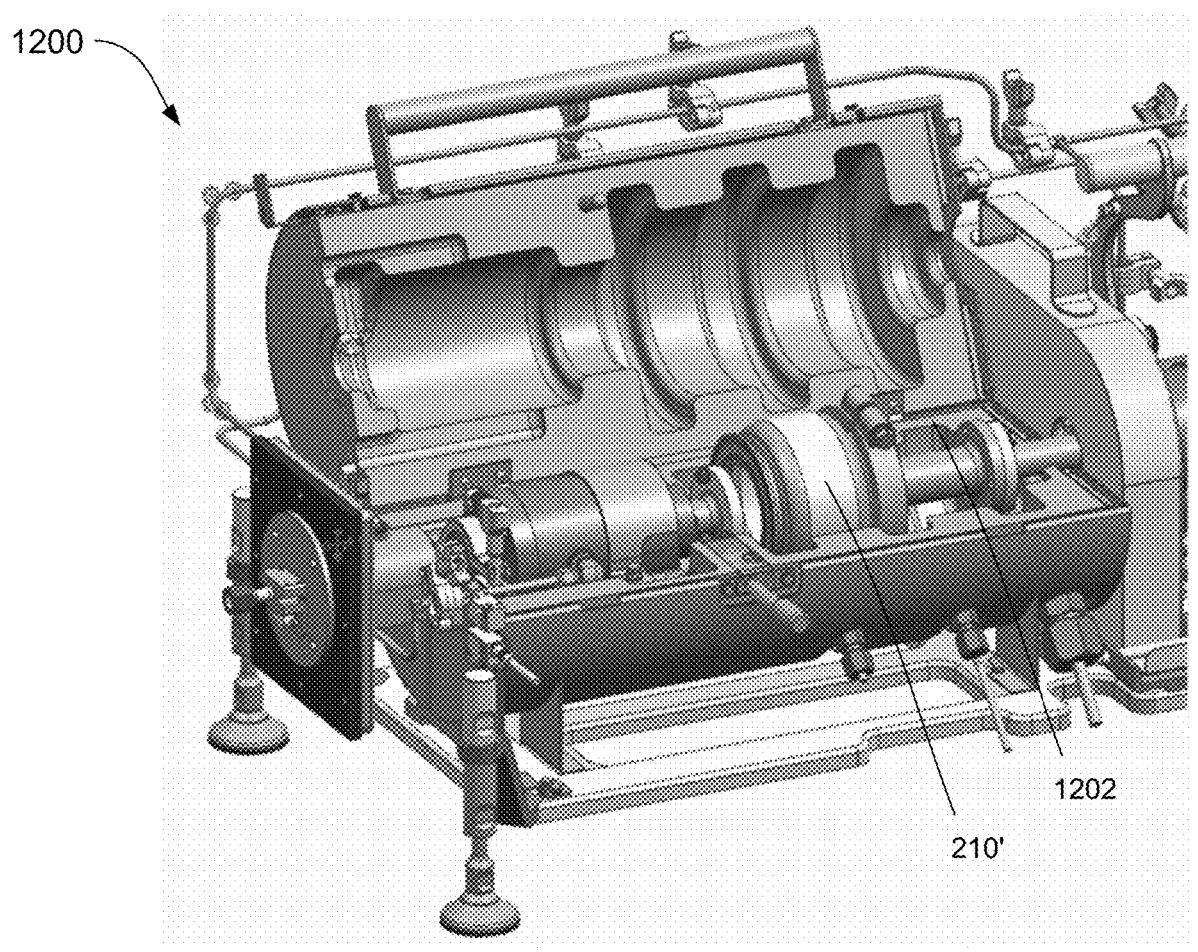
FIG. 12A depicts a reactor with a reduced volume, due to a reduced length of the drum.
Figure 12B:
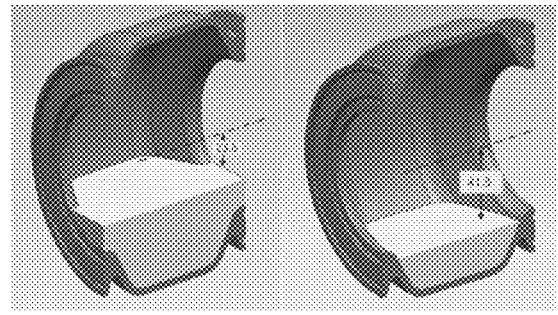
FIG. 12B depicts the drum holding different amounts of powder.

Optionally, for smaller powder loads, the length of the reactor drum 210 can be adjusted. For example, FIG. 12A depicts a reactor 1200 with a reduced volume, due to a reduced length of the drum 210'. To compensate for the reduced length, a spool 1202 can be placed in-line with the drum 210'. An update heater profile can accommodate for the shorter aperture length and can clamp at a mid-position along the aperture. In some implementations, the drum 210' can accommodate from about 0.075 to 0.22 L of powder. FIG. 12B depicts the drum 210' holding different amounts of powder, e.g., 0.22 L on the left side and 0.075 L on the right side.

Operation of Reactor System

The reactor system 200 can perform the coating using ALD and/or MLD coating conditions. The reactor system 200 permits a deposition process (ALD or MLD), to be performed at higher (above 20° C., e.g., above 50° C., e.g., 20-80° C. or 50-100° C.) or lower processing temperature, e.g., below 80° C., e.g., at or below 50° C., e.g., at or below 35° C. For example, the reactor system 200 can form thin-film metal oxides on the particles primarily by ALD at temperatures of 22-35° C., e.g., 25-35° C., 25-30° C., or 30-35° C. In general, the particles can remain or be maintained at such temperatures. This can be achieved by having the reactant gases and/or the interior surfaces of the reactor chamber remain or be maintained at such temperatures. For example, heating can be achieved by a heater cartridge embedded in chamber body, by water channel in chamber body with use of heat exchanger, or by a heater jacket on the chamber body.

Figure 8:
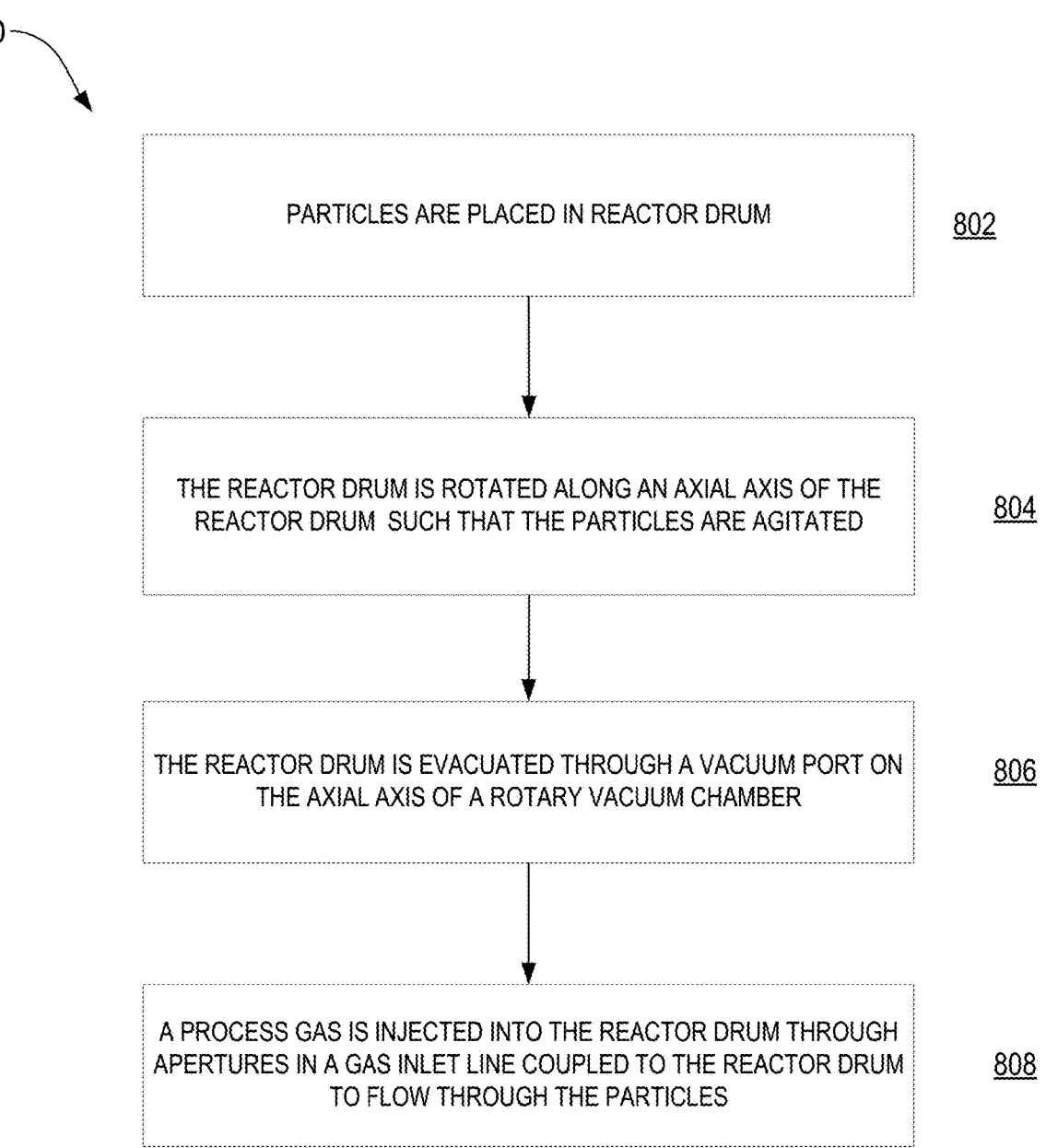
FIG. 8 is a flow diagram of an example process for utilizing the reactor system to coat particles.

FIG. 8 is a flow diagram of an example process 800 of utilizing the reactor system to coat particles. In a first step, particles are dispensed into the reactor drum, and the drum is installed in the reactor system (802).

The particles can have a solid core comprising a drug, e.g., one of the drugs discussed above. The solid core can optionally also include an excipient. Once the heating assembly 320 is in the closed position, a controller (e.g., controller 300) operates the reactor system according to a recipe in order to form the thin-film metal oxide layers and/or thin polymer layers on the particles.

The reactor drum 210 is rotated along an axial axis in a first direction so that the particles undergo a tumbling action within the drum 210 (804). The rotational speed can be 1 to 50 rpm, e.g., 6 to 50 rpm.

The reactor drum 210 is evacuated through a vacuum port, i.e., the apertures 284 in the outlet-side endplate 280 (806). Thus, a low-pressure environment can be established within the reactor drum 210, e.g., down to pressures below 1 Torr, e.g., to 1 to 500 mTorr, e.g., 50 mTorr.

A process gas is injected into the particles through the apertures 284 in the inlet-side endplate 280 (808). In some implementations, the reactor system performs an ALD and/or an MLD thin-film coating process by introducing gaseous precursors of the coating into the reactor drum 210. The gaseous precursors can spiked alternatively into the reactor drum 210. This permits the deposition process to be a solvent-free process. The half-reactions of the deposition process are self-limiting, which can provide Angstrom or nanometer level control of deposition. In addition, the ALD and/or MLD reaction can be performed at low temperature conditions, such as below 80, e.g., below 50° C., e.g., below 35° C. Flow rates of the process gas can be selected based on a type of process gas being injected. For example, a flow rate for a H₂O process gas can be 1-2 standard liters per minute (slm) of vaporized precursor for 10 kg of powder. In another example, a flow rate for H₂O process gas could range between 0.5-1 slm for powders with less surface area. In another example, TMA or TiCl₄ can have volumetric flow rates, for example, less than 1 slm. In another example, carrier gas flow rates can be, for example, in the 1-3 slm range for 10-15 kg of powder.

In some implementations, the process 800 can include additional steps, modified steps, or some of the steps can be divided into multiple steps. For example, the steps of removing, cleaning, replacing, or a combination thereof certain pieces, such as the reactor drum, of the deposition system 100 can follow step 808.

Suitable reactants for ALD methods include any of or a combination of the following: monomer vapor, metal-organics, metal halides, oxidants, such as ozone or water vapor, and polymer or nanoparticle aerosol (dry or wet). For example, chemical delivery system can provide gaseous trimethylaluminum (TMA) or titanium tetrachloride (TiCl4) as the first gas, and the second fluid can be water.

For both an ALD process and an MLD process, two reactant gases are alternately supplied to the reactor drum 210, with each step of supplying a reactant gas followed by a purge cycle in which the inert gas is supplied to the reactor drum 210 to force out the reactant gas and by-products used in the prior step.

In some implementations, the reactor system is operated in a continuous flow operation mode, e.g., for an ALD process. During an ALD process, the controller 170 can operate the reactor system as follows. In a first reactant half-cycle, while the motor 242 rotates the reactor drum 210 to agitate the particles:

i) The chemical distribution system is operated to flow the first reactant gas, e.g., TMA, into the reactor drum 210 via the apertures 284 until the particles are saturated with the first reactant gas. For example, the first reactant gas can flow at a specified flow rate and for a specified period of time, or until a sensor measures a specified first pressure or partial pressure of the first reactant gas in the reactor drum 210. In some implementations, the first reactant gas is mixed with an inert gas as it flows into the chamber. The specified pressure or partial pressure can be 0.1 Torr to half of the saturation pressure of the reactant gas.

ii) Flow of the first reactant gas is halted, and the vacuum source 250 evacuates the reactor drum 210, e.g., down to pressures below 1 Torr, e.g., to 1 to 100 mTorr, e.g., 50 mTorr.

These steps (i)-(ii) can be repeated a number of times set by the recipe, e.g., two to ten times.

Next, in a first purge cycle, while the motor 242 rotates the reactor drum 210 to agitate the particles:

iii) The chemical distribution system is operated to flow only inert gas, e.g., N₂, into the reactor drum 210 via the apertures 284. The inert gas can flow at a specified flow rate and for a specified period of time, or until a sensor measures a specified second pressure of the inert gas in the reactor drum 210. The second specified pressure can be 1 to 100 Torr.

iv) The vacuum source 250 evacuates the reactor drum 210, e.g., down to pressures below 1 Torr, e.g., to 1 to 500 mTorr, e.g., 50 mTorr.

These steps (iii)-(iv) can be repeated a number of times set by the recipe, e.g., six to twenty times.

In a second reactant half-cycle, while the motor 242 rotates the reactor drum 210 to agitate the particles:

v) The chemical distribution system is operated to flow the second reactant gas, e.g., H₂O, into the to agitate the particles via the apertures 284 until the particles 148 are saturated with the second reactant gas. Again, the second reactant gas can flow at a specified flow rate and for a specified period of time, or until a sensor measures a specified third pressure or partial pressure of the second reactant gas in the to agitate the particles. In some implementations, the second reactant gas is mixed with an inert gas as it flows into the chamber. The third pressure can be 0.1 Torr to half of the saturation pressure of the second reactant gas.

vi) The vacuum source 250 evacuates the reactor drum 210, e.g., down to pressures below 1 Torr, e.g., to 1 to 500 mTorr, e.g., 50 mTorr.

These steps (v)-(vi) can be repeated a number of times set by the recipe, e.g., two to ten times.

Next, a second purge cycle is performed. This second purge cycle with steps (vii) and (vii) can be identical to the first purge cycle, or can have a different number of repetitions of the steps (iii)-(iv) and/or different specified pressure.

The cycle of the first reactant half-cycle, first purge cycle, second reactant half cycle and second purge cycle can be repeated a number of times set by the recipe, e.g., one to ten times.

The operation is discussed above with an ALD process, but the operation is similar for MLD. In particular, in steps (i) and (v), the reactant gasses are substituted with appropriate process gasses and pressures for deposition of a polymer layer.

Moreover, although operation is discussed above with an ALD or MLD process, the system could be used for a chemical vapor deposition (CVD) process. In this case, both reactants are flowed simultaneously into the reactor drum 210 so as to react inside the chamber, e.g., during step (i). The second reactant half-cycle can be omitted.

In some implementations, the reactor system is operated in a pulsed flow operation mode, where one or more of the gases (e.g., the reactant gases and/or the inert gas) can be supplied in pulses in which the reactor drum 210 is filled with the gas to a specified pressure, a delay time is permitted to pass, and the chamber is evacuated by the vacuum source 250 before the next pulse commences. Thus, this process can be similar to the process discussed above, but the specified delay time is permitted to pass, e.g., as measured by a timer in the controller, before evacuation.

Moreover, although operation is discussed above with an ALD or MLD process, the system could be used for a chemical vapor deposition (CVD) process. In this case, both reactants are flowed simultaneously into the chamber 110 so as to react inside the chamber, e.g., during step (i). The second reactant half-cycle can be omitted.

As noted above, the coating process can be performed at low processing temperature, e.g., at or below 80° C., e.g., at or below 50° C., e.g., at or below 35° C. In particular, the particles can remain or be maintained at such temperatures during all of steps (i)-(ix) noted above. In general, the temperature of the interior of the reactor chamber does not exceed 35° C. during of steps (i)-(ix). This can be achieved by having the first reactant gas, second reactant gas and inert gas be injected into the chamber at such temperatures during the respective cycles. In addition, physical components of the chamber of the chamber can remain or be maintained at such temperatures, e.g., using a cooling system, e.g., a thermoelectric cooler, if necessary.

In some implementations, the controller can cause the reactor system 100 to first deposit a metal oxide layer on the drug-containing particles, and then deposit a polymer layer over the metal oxide layer on the particles, e.g., using the process described above. In some implementations, the controller can cause the reactor system 100 alternate between depositing a metal oxide layer and depositing a polymer layer on the drug-containing particles, so as to form a multi-layer structure with layers of alternating composition.

Removal and Installation of Reactor Drum

Returning to FIGS. 1-6, to remove the reactor drum 210 in order to process the particles therein, the operator can extend arms into the gloves 114 so as to manipulate the components discussed below. The heating assembly 320 is opened, e.g., as shown in FIG. 6, to provide access to the reactor drum 210. In addition, the drive belt 246 is loosened, e.g., by moving the tension wheel 248 out of contact with the belt 246 using the control rod 249. Next, the screws connecting the inlet-side endplate 280 to the flange of the inlet tube 220 are unscrewed, and similarly the screws connecting the outlet-side endplate 280 to the flange of the outlet tube 230 are unscrewed. The assembly of the outlet tube 230, wheel 244, and rotary outlet seal 234 can then be shifted along the axis of rotation away from the reactor drum 210. Some other components may need to be loosened to enable this motion.

Referring to FIG. 9, a handle assembly 350 is placed to hold the reactor drum 210. The handle can include two components, each with an arcuate portion that will contact the outer surface of the reactor drum. In particular, while the reactor drum 210 is still sitting within the heating assembly, the arcuate portion 354 of the first component 352 (see FIG. 9A) is inserted between the drum 210 and lower half-cylinder 322 and slid around until a clamping plate 356 is near the where the blocks 322, 324 are hingedly connected. Then the arcuate portion 364 of the second component 362 (see FIG. 9B) is inserted between the drum 210 and lower half-cylinder 322 on the opposite side from the first component 352. The clamping plate 356 of the first component is secured to a handle 366 extending from an end of the arcuate portion 364 of the second component. For example, screws can fit through holes 368 in the handle 366 into threaded receiving holds in the clamping plate 356. The arcuate sections now completely surround the reactor drum 210 without the drum having been moved. The reactor drum 210 can now be lifted out using the handle 366.

Additional caps 370 can be installed over the endplates 280 to cover the apertures to prevent escape of particles. At this point, the reactor drum 210 with caps 370 could be placed into the detachable transfer container 130 of the rapid transfer port.

However, some operators may wish to transfer the coated particles out of the reactor drum while still within the isolator. In this case, referring to FIG. 10A, the reactor drum 210 can be placed on a powder loading/unloading fixture 380. The fixture 380 can include a stand 382 that can sit on the platform in the isolator and that supports a rotatable support 384. As shown in FIG. 10A, the reactor drum 210 can be placed onto the fixture 380 in a horizontal orientation. As shown in FIG. 10B, the support 384 can be rotated 90 degrees. The caps 370 and endplate 280 now at the top of the reactor drum 210 is removed from the cylindrical tube 270, and a canister 20 is secured to the open top end of the cylindrical tube 270. Then, as shown in FIG. 10C, the support is rotated by 180 degrees, permitting the coated particles inside the reactor drum 210 to fall into the canister 20. The canister 20 can then be removed from the reactor drum 210, a lid can be placed on the canister 20, and the canister 20 can be placed in the detachable transfer container 130 of the rapid transfer port.

To load into the reactor drum 210, the above operations can be performed in reverse using uncoated powder.

CONCLUSION

The controller 300 and other computing devices part of systems described herein can be implemented in digital electronic circuitry, or in computer software, firmware, or hardware. For example, the controller can include a processor to execute a computer program as stored in a computer program product, e.g., in a non-transitory machine readable storage medium. Such a computer program (also known as a program, software, software application, or code) can be written in any form of programming language, including compiled or interpreted languages, and it can be deployed in any form, including as a standalone program or as a module, component, subroutine, or other unit suitable for use in a computing environment. In some implementations, the controller 300 is a general purpose programmable computer. In some implementations, the controller can be implemented using special purpose logic circuitry, e.g., an FPGA (field programmable gate array) or an ASIC (application specific integrated circuit).

For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions. The present disclosure provides apparatus for and methods of preparing pharmaceutical compositions comprising API containing particles encapsulated by one or more layers of metal oxide and/or one or more layers of a polymer. The coating layers are conformal and of controlled thickness from several nanometers to several micrometers in total. The articles to be coated can be composed of only API or a combination of API and one or more excipients. The coating process described herein can provide an API with an increased glass transition temperature for the API relative to uncoated API, a decreased rate of crystallization for an amorphous form of the API relative to uncoated API, and decreased surface mobility of API molecules in the particle compared to uncoated API. Importantly, particle dissolution can be altered. Because the coating is relatively thin, drug products with high drug loading can be achieved. Finally, there are benefits with respect to cost and ease of manufacture because multiple coatings can be applied in the same reactor.

Terms of relative positioning are used to refer to relative positioning of components within the system or orientation of components during operation; it should be understood that the reactor system could be held in a vertical orientation or some other orientation during shipping, assembly, etc.

A number of embodiments of the invention have been described. Although the application has focused on a reactor including a rotatable drum, the features described could be incorporated into reactors that use a stationary drum with rotating paddles therein, or other types of reactors. It will be understood that various modifications may be made without departing from the spirit and scope of the invention.

What is claimed is:

1. A reactor for coating particles, comprising:
   a rotatable reactor assembly including a reactor drum configured to hold a plurality of particles to be coated, an inlet tube, and an outlet tube, wherein the drum includes a cylindrical tube, and an inlet-side endplate secured to cover an inlet-side opening of the cylindrical tube and/or an outlet-side endplate secured to cover an outlet-side opening of the cylindrical tube, wherein the cylindrical tube provides an exposed featureless cylindrical interior surface extending from the inlet-side endplate to the outlet-side endplate for contact with the particles;
   a stationary gas inlet line coupled to the inlet tube by a rotary inlet seal;
   a stationary gas outlet line coupled to the outlet tube by a rotary outlet seal; and
   a motor to rotate the rotatable reactor assembly;
   wherein the inlet tube is releasably mechanically secured to the inlet-side endplate and the outlet tube is releasably mechanically secured to the outlet-side endplate.

2. The reactor of claim 1, wherein the inlet tube comprises an outwardly extending annular inlet tube flange and the outlet tube comprises an outwardly extending annular outlet tube flange.

3. The reactor of claim 2, wherein the inlet tube flange is releasably mechanically secured to the inlet-side endplate and the outlet tube flange is releasably mechanically secured to the outlet-side endplate.

4. The reactor of claim 3, wherein the inlet tube flange is screwed onto the inlet-side endplate and the outlet tube flange is screwed onto the outlet-side endplate.

5. The reactor of claim 1, comprising one or more gaskets, each gasket clamped between one of the tubes and a respective one of the endplates.

6. The reactor of claim 1, further comprising a heater to radiatively heat at least the reactor drum.

7. The reactor of claim 6, further comprising controller configured to cause the heater to control a temperature within the drum to be within a range between 20 to 80 degrees Celsius.

8. The reactor of claim 6, wherein the heater comprises a lower half-cylinder and an upper half-cylinder that is liftable away from the lower half-cylinder, and a heating element to heat the lower half-cylinder and upper half-cylinder.

9. The reactor of claim 8, wherein the upper half-cylinder and lower-half cylinder are connected along one edge to open in a clam-shell manner.

10. The reactor of claim 8, wherein each of the lower half-cylinder and upper half-cylinder extend across the drum, inlet tube, and rotary inlet seal.

11. The reactor of claim 10, wherein each of the lower half-cylinder and upper half-cylinder do not extend across and rotary outlet seal.

12. The reactor of claim 11, comprising a drive wheel coupled to the outlet tube, and wherein an outlet-side edge of the heater is between the drive wheel and the reactor drum.

13. The reactor of claim 8, wherein the heating element comprises one or more resistive heaters embedded in or attached to the lower half-cylinder and upper half-cylinder.

14. The reactor of claim 8, wherein the lower half-cylinder and upper half-cylinder comprise solid metal bodies.

15. The reactor of claim 14, wherein the lower half-cylinder and upper half-cylinder comprise aluminum.

16. The reactor of claim 8, wherein the lower half-cylinder and upper half-cylinder have an inner surface shaped to not contact the rotatable reactor assembly.

17. The reactor of claim 16, wherein the inner surface is shaped to conform to the rotatable reactor assembly.

18. The reactor of claim 17, wherein the inner surface is shaped to provide a uniform distance between the inner surface and an outer surface of rotatable reactor assembly along an axis of rotation of the drum.

* * * * *